July 11, 1961 G. MERRILL Plant Pat. 2,071
PEACH
Filed Oct. 10, 1958
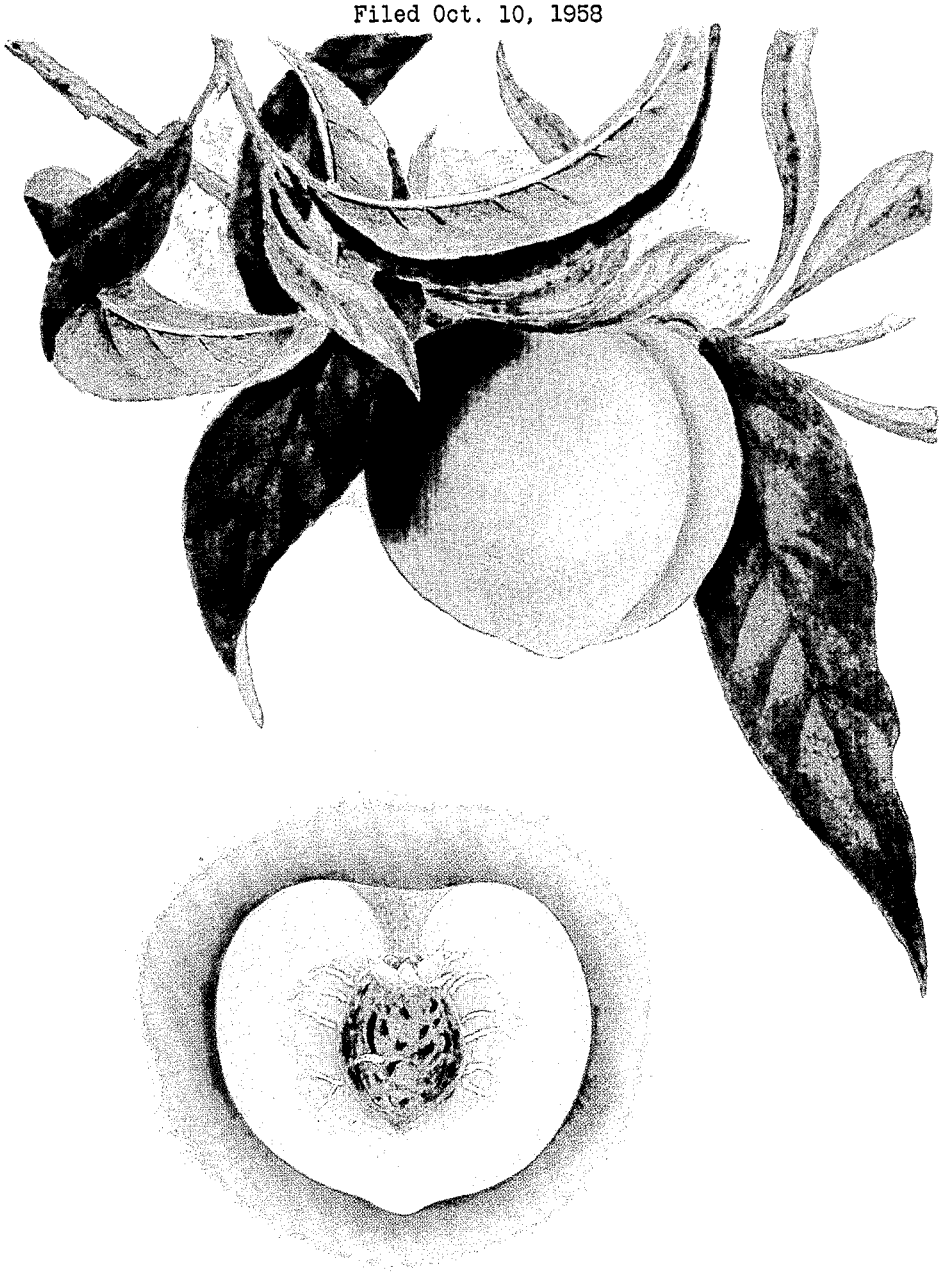
WITNESS
Addison E Avery
INVENTOR
GRANT MERRILL
ATTORNEYS
HUEBNER & WORREL
BY Richard M. Worrel United States Patent Office Plant Pat. 2,071
Patented July 11, 1961

2,071
PEACH

Grant Merrill, P.O. Box 392, Red Bluff, Calif.

Filed Oct. 10, 1958, Ser. No. 766,639
1 Claim. (Cl. 47—62)

This invention relates to a new and distinct variety of peach which bears large, round, yellow fleshed, firm, freestone peaches, with red coloring over about half of the surface of the fruit as grown in California, and ripening about twenty to twenty five days after Elberta (unpatented), and blooming about in midseason for peaches, and with self fertile blossoms.

In comparison with Merrill Splendor (Plant Patent No. 1,257) the instant variety of peach has self fertile blossoms, blooms earlier, ripens about five days later, and the fruit is somewhat more highly colored.

I originated the present variety of peach tree on my farm near Red Bluff, Tehama County, California in the following manner:

A number of seeds of the J. H. Hale (unpatented) peach tree, which resulted from open pollination, were selected by me, germinated, and the resultant seedlings grown until they flowered, were open pollinated, and produced fruit. From said fruit a number of seeds were again selected, germinated, and the resultant seedlings grown until they in turn produced fruit. This procedure was repeated for four generations, in each instance relying on open pollination; selecting fruit for high color, firmness and size as well as on the basis of health and vigor of the trees producing the fruit; and germinating only the seeds from the carefully selected fruit.

In the fourth generation ($F_4$) the instant variety first fruited in July 1954 and its fine qualities were noted. Asexual reproductions were performed by me, as follows: In 1956, the instant variety was budded onto young peach trees on my farm at Red Buff, Tehama County, California. In addition, in March 1957, scion wood of the instant variety was budded into two trees of the Merrill June (Plant patent No. 869) growing on my farm near Lamont, Kern County, California. When these trees came into bearing, it was found that in both aforementioned cases of asexual reproduction the fruit and the tree characteristics were the same as those of the original selected fourth generation seedling in all observed respects.

The accompanying drawing shows a characteristic twig of the subject variety bearing foliage and a mature fruit as well as such a fruit divided on its suture plane to reveal flesh and pit characteristics.

Referring now more specifically to the promological details of the instant variety of peach tree, the following is an outline description thereof; all major color plate identifications being by reference to Maerz and Paul Dictionary of Color:

*Tree*

Medium size, medium vigor, medium upright, medium dense, vase formed by pruning, hardiness unknown, productive, regular bearer.

Trunk: Medium stocky, medium shaggy.

Branches: Main branches grey and medium shaggy when older, moderately smooth and brown when younger. Lenticles—medium few, medium size.

Leaves: (Selected from midportion of vigorous unbranched terminal shoots 18" to 24" long.) Length—6" to 6¾"; average, 6 5/16". Width—1⅜" to 1⅝"; average, 1½". Medium size.

*Form.*—Lanceolate, tip acuminate, medium thick.

*Leaf color.*—Upper surface, medium green (23–L–2), under surface lighter green (22–K–5), midrib lighter green (10–J–1).

*Class* (Meader and Blake: Proceedings Am. Soc. Hor. Sc., vol. 37, page 206).—2 and 3. Width—length ratio, .24. Apex Angle—27° to 32°; average, 29½°. Base Angle—73° to 86°; average, 81½°.

*Margin.*—Crenate.

*Petiole.*—Medium long, medium slender.

*Glands.*—Mostly two to four. Opposite and alternate medium size, reniform, yellowish green, position, on petiole and base of leaf.

*Stipules.*—On base of leaf, falling off early.

Flower buds: Hardiness unknown, medium size, truncate to obtuse, plump, free, pubescent.

Flowers: Medium early, pink, small.

*Fruit*

Maturity when described, firm ripe.

Size: Variable.

*Axial diameter.*— 2¾" to 3"; average, 2 13/16".

*Transverse in suture plane.*— 2⅞" to 3⅜"; average, 3 3/16".

*At right angles to suture plane.*—3" to 2½"; average, 3 3/16".

Form: Globose to slight compressed axially.

*Suture.*—Inconspicuous to distinct line, extends from base to beyond but discontinuous at apex. Has slight depression beyond pistil point.

*Ventral surface.*—Rounded but slightly lipped on one side.

*Cavity.*—Flaring, elongated in suture plane with suture showing on both sides. Depth, 7/16" to 9/16"; average, ½". Breadth, ¾" to 1"; average, ⅞". Markings—light yellow ground color, red blush.

*Base.*—Rounded to truncate.

*Apex.*—Short, rounded.

*Pistil point.*—Apical.

*Stem.*—Length, ⅜"; diameter, ⅛". Adheres to stone on a few, especially when not full ripe.

*Skin.*—Medium thick medium tender, frees from flesh when soft ripe, tendency to crack, none. Color—yellow (10–L–6) to darker yellow (11–I–10) with red markings (4–L–10) to (6–L–10) to darkest red blush (7–L–12).

Flesh: Light yellow (9–L–4) to darker yellow (10–J–8), red at stone (4–L–4) to (6–L–6) farther from stone. Surface of pit cavity, light red, wtih light red fibers.

*Amygadalin.*—Scant.

*Juice.*—Moderate.

*Texture.*—Extra firm, meaty, somewhat fiberous.

*Fibers.*—Abundant but tender.

*Ripens.*—Evenly.

*Flavor.*—Mild sub acid.

*Aroma.*—Wanting.

*Eating quality.*—Fair.

Stone: Free, adheres to flesh along suture plane at times when firm ripe sometimes elsewhere. Fibers, long, distinct, tender.

*Size.*—Medium small, quite reqular. Length, 1 5/16" to 1½"; Average 1⅜". Breadth, ⅞" to 1 1/16"; average, 1". Thickness, ¾" to ⅞"; average, 25/32".

*Form.*—Obovate.

*Base.*—Mostly oblique, some straight.

*Hilum.*—Oval.

*Apex.*—Mucronate.

*Sides.*—Fairly regular.

*Surface.*—Pitted through central parts and pitted toward apex, grooved on sides and toward base. Ventral edge—mostly small grooves, discontinuous. Dorsal edge—mostly two ridges, usually interrupted, almost always interrupted near tip.

*Color.*—Brown (7–A–12). Particles of flesh occasionally protrude from holes in the stone.

*Tendency to split.*—None

Use: Market, local, dessert, culinary, long distance shipping.

Keeping quality: Good.

Shipping quality: Good.

*General notes*

The tree and its fruit herein described may vary some due to climatic and soil conditions under which the variety may be grown, and the method of growing, including fertilizing, pruning, thinning, the pest and diseases present on the tree, and other causes.

Having illustrated and described my new peach tree, I claim.

A new and distinct variety of peach tree substantially as herein illustrated and described which ripens approximately twenty to twenty-five days after Elberta (unpatented); which produces large, yellow-fleshed, freestone fruit of distinctive red color and round shape, particularly characterized by unusual firmness of its flesh; and which resembles the Merrill Splendor (Plant Patent No. 1,257) but is distinguished therefrom in blossoming somewhat earlier, being self fertile and having fruit that is redder in color and ripens approximately five days later.

No references cited.